---

United States Patent [19]
Vickery

[11] 3,991,750
[45] Nov. 16, 1976

[54] DROMOSTANOLONE PROPIONATE IMPLANT PELLET USEFUL FOR PRODUCING WEIGHT GAINS IN ANIMALS AND SUPPRESSING ESTRUS IN FEMALE ANIMALS

[75] Inventor: Brian H. Vickery, Cupertino, Calif.

[73] Assignee: Syntex Corporation, Palo Alto, Calif.

[22] Filed: Apr. 28, 1975

[21] Appl. No.: 572,691

[52] U.S. Cl. .............................. 128/260; 128/272; 128/130
[51] Int. Cl.² ....................... A61M 7/00; A61J 1/00
[58] Field of Search .......... 128/260, 272, 130, 264; 119/51 R, 1; 424/19, 21, 22; 260/379.4

[56] References Cited
UNITED STATES PATENTS

| | | | |
|---|---|---|---|
| 3,118,915 | 1/1964 | Ringold | 128/260 UX |
| 3,608,549 | 9/1971 | Merrill | 128/260 |
| 3,710,795 | 1/1973 | Higuchi | 128/260 |
| 3,857,932 | 12/1974 | Shepherd | 128/260 X |
| 3,867,519 | 2/1975 | Michels | 128/260 X |
| 3,870,791 | 3/1975 | Haddad | 128/260 X |

Primary Examiner—Aldrich F. Medbery
Attorney, Agent, or Firm—Tom M. Moran

[57] ABSTRACT

Dromostanolone propionate has been found to result in a surprisingly large increase in weight in animals when administered as a pellet implant. In female animals, e.g. heifers, estrus is also suppressed. A particularly effective implant pellet exhibits a substantially constant rate of drug delivery over a first time period and an abrupt termination of drug delivery at the end of said time period, thus eliminating the need to surgically remove the implanted pellet to stop administration of the drug to the animal.

38 Claims, 4 Drawing Figures

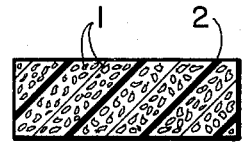 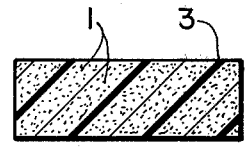
FIG_1  FIG_2
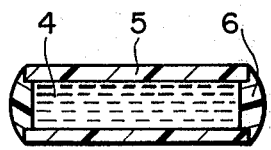 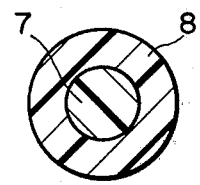
FIG_3  FIG_4

DROMOSTANOLONE PROPIONATE IMPLANT PELLET USEFUL FOR PRODUCING WEIGHT GAINS IN ANIMALS AND SUPPRESSING ESTRUS IN FEMALE ANIMALS

FIELD OF THE INVENTION

One aspect of this invention relates to a novel, subcutaneously implantable pellet which comprises an effective amount of dromostanolone propionate in combination with an effective amount of a biocompatible carrier. Preferably the pellet exhibits a substantially constant rate of drug release over first time period and an abrupt termination of drug release at the end of that time period. Other aspects of the invention include processes for inducing weight gain or suppressing estrus by implanting the novel pellet of this invention in an animal for a suitable period and feeding the animal normally. The various aspects of this invention are particularly valuable in the process of raising domestic livestock, especially heifers.

PRIOR ART

Dromostanolone propionate (the 17-propionate of 2α-methylandrostan-17β-ol-3-one) is known from U.S. Pat. No. 3,118,915 and it is alleged therein that the series of related compounds possess anabolic and antiestrogenic activity. The compound is recommended for use in palliative treatment of advanced or metastatic carcinoma of the breast of women (Physicians Desk Reference, 29th Ed, 1975). The compound, when administered orally, does not show sufficient activity for the commercial application of the compounds to be utilized in the diet of animals for weight gain. It has not been known to use the compound as a solid implant. It has now been discovered that a subcutaneously implantable pellet containing dromostanolone propionate gives unexpectedly superior weight gain and estrus suppression in animals, especially heifers.

A general discussion of recent theories behind absorption of implanted solid drugs is found in "Absorption of Implanted Solid Drug", Burton E. Ballard and Eino Nelson, *J. P. Pharm. Sci.*, Vol. 51, No. 10, pp. 915–924, October, 1962. A more general discussion is found in *Remington's Pharmaceutical Sciences*, 14th edition, Chapter 89, "Prolonged-Action Pharmaceuticals". Generally implantable pellets will either be a diffusion matrix, dissolution pellet, or diffusion barrier, formulation.

Examples of diffusion matrix implants may be found in U.S. Pat. No. 3,565,991 to Short; 3,577,512 to Sheppard et al.; and 3,737,521 to Born. In these patents a drug is dispersed throughout a polymer which is implanted in the body and this drug is leached or diffuses from the polymer matrix in which it is dispersed. Generally the diffusion matrix formulation results in the release rate of the drug which may be substantially constant over a first period of time but which eventually diminishes as the drug is released from the formulation. In many formulations of this type substantial amounts of drug may remain in the matrix even after it has become inactive.

Representative descriptions of dissolution pellet formulations may be found in U.S. Pat. No. 3,428,729 to Anderson et al. and U.S. Pat. No. 2,895,875 to Klette. The Anderson et al. patent is a DES implant formulation which shows a decreasing rate of release, whereas the Klette patent discloses an implant which comprises an inner core of coarse hormone crystals surrounded by a layer of smaller water soluble hormone crystals in a binder such as methycellulose. The Klette invention results in a shock like effect when the outer small particles are quickly dissolved in the body fluid but a prolonged effect due to the coarse inner crystals. Thus, there are two entirely different rates of release, whereas in a preferred aspect of this invention, a substantially constant release rate may be obtained. Dissolution pellets exhibit the disadvantage of a decreasing rate of release as time progresses. Also more drug is utilized in the pellet than is delivered at an effective level because of the decreasing rate.

An example of a diffusion barrier implant may be found in U.S. Pat. No. 3,279,996 to Long and Folkman. In this design a drug is placed in the lumen of a tube of polydimethylsiloxane and the ends of the tube are sealed. The tubing wall thickness and surface area of the tube determine the rate of release for a given drug.

Diethylstilbestrol (DES) is known to be an anabolic agent and has been used as an implant to produce increased weight gain in steers and heifers of about 10 to 15% over untreated animals. It is further known that SYNOVEX S and SYNOVEX H, which contain steroids, progesterone and estradiol benzoate, also produce weight gain in steers and heifers of about the same range, that is 10 to 15%. Other implant products which have been commercialized include FINAPLIX, an implant containing triembolone acetate sold in France, and RALGRO, an implant containing a resorcylic acid lactone marketed by commercial Solvents Corp. in the United States. The DES and RALGRO products are non-steroid products chemically unrelated to dromostanolone propionate and are mentioned here only to show the state of the commercially available implant art.

It has now been discovered that the use of a pellet implant containing dromostanolone propionate gives an unexpectedly superior weight gain and feed efficiency and can produce from 2 to 5 times the weight gain in heifers seen with the most closely related commercial product. Preliminary studies have shown that the weight gain in heifers may be up to about 60% of the gain compared to a control animal over the same period of time. Not only is a greater weight gain and feed efficiency seen using dromostanolone proprionate implant, but also the additional weight does not appear to be disproportionate in the amount of fat or water that is laid down in the meat, contrary to the results seen with other commercial products.

When used to produce weight gain in heifers, the most closely related commercial product SYNOVEX H, also enhances estrus. This is disadvantageous since the heifers will not gain as much weight because of the additional activity of the animals while they are in heat. The use of dromostanolone propionate implant in heifers, on the other hand effectively suppresses estrus.

Products are known in the art which are useful for estrus suppression. For example U.S. Pat. No. 3,499,445 to Reed points out that steroids such as chlormadinone acetate, dimethisterone, ethisterone, hydroxyprogesterone and others may be formulated as implants which, when implanted in the female animal, act to block estrus. However, the Reed patent requires that the implanted pellet be surgically inserted into the female and permitted to remain in the animals for 14 to 18 days to prevent estrus after which time the pellet is surgically removed to halt the medication and thus induce the onset of estrus. Thus, it is clear that the Reed product is not intended for weight gain simultaneously with estrus suppression.

The dromostanolone propionate implant pellet of this invention may be used to produce weight gain while suppressing estrus at the same time. Further, this invention may be formulated so that it can be implanted for a first time period during which time a constant rate of drug is released and at the end of which time the release is abruptly terminated, thus allowing the onset of estrus following the termination of the release of the drug, without surgically removing the pellet implant.

Another disadvantage of the Reed patent is that the disc which is used for implanting must be protected by a pellet encasement device, whereas the pellet of this invention need not have such a device to protect it but may be injected directly into the animal.

Belgian Pat. No. 818,572 teaches an implant which comprises (A) at least one sex hormone or anabolic agent having a hydroxy function, (B) at least one carboxylic acid ester of A, and (C) a suitable solid excipient. The Belgian Patent makes no specific reference to the unique, unexpectely superior properties of a dromostanolone propionate implant pellet and, contrary to the Belgian Patent, the implant of this invention produces its unexpected superior results with dromostanolone propionate alone and requires no combination with another anabolic or estrus suppressing agent having a hydroxy function. It should be noted that the Belgian Patent is mentioned to show the state of the art, but is not to be considered prior art under 35 U.S.C. 103 through 35 U.S.C. 102 because, i.a., the publication of the Belgian patent does not appear to be sufficient to qualify as a 103 reference.

Thus, this invention has the following advantages over known, available products and processes:
1. Unexpectely superior weight gain in animals treated;
2. Estrus suppression accompanying weight gain;
3. Pellet implantable using simple injection techniques, surgery not required;
4. Pellet does not require protective device; and
5. combinations with other drugs not required; and the pellet implant may be formulated in a unique manner to-
6. Exhibit substantially constant drug release for better control of drug administration;
7. Exhibit abrupt termination of drug release obviating the need to remove the pellet to induce estrus;
8. Synchronize estrus in a plurality of female animals using simple injection techniques, and
9. Utilize less total drug to achieve improved weight gain and/or estrus suppression than other pellet formulations.

SUMMARY OF THE INVENTION

The primary aspect of this invention is a solid, subcutaneously implantable pellet which comprises a biologically effective amount of the 17-propionate of 2α-methyl-androstan-17 -ol-3-one in combination with an effective amount of a biocompatible carrier. Preferably, the pellet exhibits a substantially constant rate of release of the drug over a first time period and a substantially abrupt termination of release of the drug at the end of that period. The preferred design for constant rate release pellet comprises (a) a biocompatible, inert, spherical core having a diameter of about 2 mm. to about 10 mm. and (b) at least one uniform biocompatible, biosoluble coating about 0.05 mm. to about 1.0 mm. in thickness surrounding the core, the coating being a homogenous mixture of the propionate and a suitable carrier, preferably a polyethylene glycol of 3,000 to 20,000 molecular weight. Preferred embodiments of the pellet are set forth hereinafter.

Another aspect of this invention is the subcutaneous implantation of the pellet to effect surprisingly large weight gains in animals, especially bovines and more particularly heifers. When subcutaneously implanted, the animals may also be prevented from coming into heat.

The preferred pellet formulation exhibiting a constant rate of release is prepared by utilizing a particular combination of solvents in the process of coating the inert cores.

BRIEF DESCRIPTION OF THE DRAWINGS

FIG. 1 is a vertical cross section of a diffusion matrix implantable pellet.

FIG. 2 is a vertical cross section of a dissolution type implantable pellet.

FIG. 3 is a vertical cross section of a diffusion barrier implantable pellet.

FIG. 4 is a vertical cross section of the inert core implantable pellet.

PREFERRED EMBODIMENTS

Pellet Composition

The primary aspect of this invention is premised on the discovery that dromostanolone propionate, that is the 17-propionate of 2α-methyl-androstan-17β-ol-3-one which is represented by the following formula

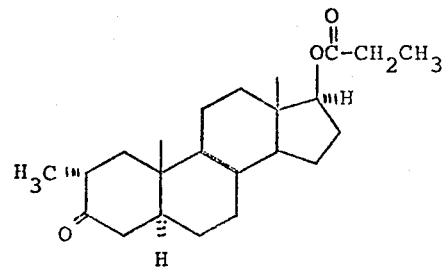

when used as the sole active ingredient in a solid pellet implant in animals results in an unexpectedly large increase in weight in the animals. In heifers, the weight gain may be about 2 to 5 times that which can be obtained by the most closely related known commercial product such as an implant of SYNOVEX H. Not only is the pellet implant of this invention superior with regard to anabolic results but it also suppresses estrus at the same time. This is contrary to other commercial products which enhance estrus while resulting in weight gain.

Broadly the invention may be visualized as a solid, subcutaneously implantable pellet which comprises a biologically effective amount of dromostanolone propionate in combination with an effective amount of a biocompatible carrier. The pellet may be diffusion matrix, diffusion barrier, or dissolution pellet type. Thus the dromostanalone propionate may be combined with any of the carriers which are known for use in preparing subcutaneously implantable pellets.

In the case of diffusion matrix pellets as shown in FIG. 1, such carriers are generally non-toxic, biocompatible polymers and include acrylic acid polymers, methacrylic acid polymers, other alkacrylic acid polymers, polyurethane, silicone rubber (e.g. Silastic), polysiloxane, block SBR copolymers, PVC polymers, and the like. In FIG. 1, the dromostanolone propionate 1 is dispersed throughout the polymer 2. For example a suitable Silastic (Trademark for a silicone rubber) matrix may contain 5–50%W of dromostanolone propionate, 50–95%W Silastic 382 elastomer or some other suitable silicone rubber, and 0–30% suitable diluent such as 360 Medical Fluid (Dow-Corning).

On the other hand the dromostanolone propionate may be formulated to form a dissolution pellet which may be less than 100% active ingredient and will contain an effective amount of a carrier such as a solid polyethylene glycol. In FIG. 2, a cross section of a dissolution pellet having dromostanolone propionate 1 in a carrier 3 is shown. Other carriers include methyl cellulose, cholesterol, a biocompatible high molecular weight fatty acid such as stearic acid or a metal stearate such as magnesium stearate, a solid biocompatible wax, carboxymethocellulose, polyvinylpyrrolidone, and the like or mixtures thereof. Particularly suitable as a carrier is a solid polyethylene glycol (PEG) having a molecular weight from 3,000 to about 20,000, e.g. PEG 6000–7500 (CARBOWAX 6000). An effective amount of carrier is that amount necessary to maintain the structural integrity of the pellet when implanted in the amimals body. Generally, at least 0.5%w of the carrier will be required. Thus the pellet will comprise about 0.5–99% carrier and about 1% to 99.5% dromostanolone propionate, preferably the pellet will contain at least 50% of the active ingredient. A representative formulation may contain 50–95% dromostanolone propionate, 5–50% PEG 6000, and 0–1% magnesium stearate. U.S. Pat. No. 3,428,729 to Anderson et al utilizes bees wax, zinc stearate dibutylphthalate and polyvinylpyrrolidone.

A representative diffusion barrier formulation is described in U.S. Pat. No. 3,279,966 to Long et al, and as much of that patent as is pertinent is incorporated herein by reference. FIG. 3 shows a vertical cross section of a diffusion barrier formulation where the mixture 4 of dromostanolone propionate and a suitable dispersing agent is enclosed by tube 5 having sealed ends 6. Such a formulation may be prepared by mixing about 50–100% dromostanolone propionate with about 0–50% of a suitable dispersing agent as Polysorbate 80 and placing the resulting mixture in a suitable polysiloxane tube (Silastic Medical grade tubing) and sealing the ends of the tube with a suitable polysiloxane adhesive (Silastic Medical grade). The tubing may be any suitably implantable size.

The shape of the pellet may be any of the typical shapes which are used for subcutaneous implanted materials such as a disc, a cylinder, a sphere, or an egg shape. However, because of the ease of preparation and the reaction of the body to sharp corners of implants the implant should be substantially free of sharp edges.

A biologically effective amount of dromostanolone propionate is that amount needed to effect the desired result, that is weight gain or estrus suppression, when implanted either alone or in combination with other similar pellets. The amount delivered to the animal will depend on the animal, pellet design, carrier, etc., and may vary over a broad range. Generally the dromostanolone propionate is present in the pellet in an amount from 1% by weight to about 99.5% by weight of the pellet and the biocompatible carrier is present from about 0.5% by weight to about 99% by weight of the pellet. Formulation can be varied substantially but preferably the pellet will have at least 20% by weight of the active ingredient while the remainder of the pellet will be the carrier. The rate of release of drug depends, at least in part, on the kind and amount of carrier employed. For example, a fast release dissolution type pellet may be prepared using PEG 6000–7500, the release rate increasing with PEG 6000–7500 concentration.

It has been found that it is preferable to formulate a pellet which exhibits a substantially constant rate of drug delivery over the time period desired. This may be done using any formulation known in the art which results in a substantially constant rate of drum release, e.g. the silicone rubber implant disclosed in U.S. Pat. No. 3,279,996 to Long et al. In such a formulation the dromostanolone propionate is enclosed in a capsule of silicone rubber through which dromostanolone propionate diffuses at a constant rate.

Preferably, however, constant release rate along with abrupt termination of drug release is obtained by the unique pellet implant design, heretofore unknown in the art. Such a pellet is shown in vertical cross section in FIG. 4 where an inert core 7 is uniformly coated with a layer of a substantially homogeneous mixture 8 of the drug in a carrier. Because of the importance of precise formulation and performance in the animal the shape is of the inert core and the resulting implant is spherical. Thus, a spherical inert core is layered with a uniform layer of drug in a carrier in order to form a spherical product which exhibits the constant rate release and abrupt termination as desired. The drug-carrier combination is a homogeneous mixture which may be a solid solution, dispersion, or suspension or a combination, but the drug is uniformly distributed in the coating. Generally the carrier used will be not only a binder for the drug, that is, its properties will be such that the mixture of the two will properly adhere to the inert core and maintain the structural integrity of the pellet, but also the carrier will be a dissolution rate modifier for the dromostanolone propionate, that is, the carrier will affect the rate of release of the drug from the sphere. Depending on the carrier the drug may be absorbed at a faster rate or slower rate than the drug would be absorbed if it were coated on the sphere alone. For example, a PEG generally speeds up the rate of dissolution while cholesterol generally slows down the rate of dissolution.

The carrier which may be utilized in the coating of this invention may be any suitable carrier but of course must be biocompatible with the animal which is being treated, that is it may not be toxic to the animal or otherwise adversely affect the metabolism of the animal. Further, the coating must be biosoluble, that is it must dissolve in the body fluids which act upon the pellet where it is implanted in the body. Thus, it can be seen that the carrier which is used to coat the inert sphere is a binder as well as a dissolution rate modifier for the drug. It is a binder in that it must properly adhere to the inert core while maintaining the structural integrity of of the coating and is a dissolution rate modifier in that it effects the rate at which the drug is released from the implanted core.

Representative carriers which may be used for the purpose of this invention include cholesterol, solid polyethylene glycols, high molecular weight fatty acids such as stearic acid, biosoluble waxes, solid carboxymethocellulose, and solid polyvinylpyrrolidone. Depending upon the carrier and drug combination used, the drug may be absorbed at a faster or slower rate than the drug would be if it were coated on the sphere alone. For example, polyethylene glycols generally speed up the rate of release while cholesterol generally slows down the rate of release for many drugs. Because of availability, compatibility with most animals, and adherence properties, solid polyethylene glycols having molecular weights of about 3,000 to 20,000, especially PEG 6000–7500 such as CARBOWAX 6000.

For proper adherence to the inert core at least about 5% of the carrier is needed in the uniform outer coating, and to obtain a therapeutically effective dose of the drug at least about 10% of the coating should be dromostanolone propionate. A preferred range of the composition of the outer coating is about 20%w to about 90%w dromostanolone propionate and about 5%w to about 80% of the carrier. Particularly preferred is a mixture of about 30%w to about 90%w dromostanolone propionate and about 10% to about 70% of the carrier.

The inert core may be a non-dissolving material such as a polymeric material represented by cellulose acetate, methylmethacrylate or other acrylics, polypropylene, polysiloxane, and nylon. Other non-dissolving materials include glass and biocompatible metals. On the other hand the inert core may be made of a non-toxic dissolving material such as POLYOX (Union Carbide), KLUCEL (Hercules), or sugar-starch beads. The advantage of the dissolving cores is that once the drug from the outer coating is released, the animal is able to absorb the non-toxic dissolving material to the point where the implanted pellet dissolves substantially, completely obviating the need to remove the pellet if the animal is slaughtered. In that case, a dissolving core is preferred.

Because of ease of formulation and application the biocompatible, inert, spherical core particularly suited for this invention exhibits a diameter of about 2 mm to about 10 mm and preferably between about 2 mm to about 3 mm.

To maintain a substantially constant rate of release in the preferred, inert core formulation of this invention, the diameter of the inert core is at least half the diameter of the final spherical implant and preferably will be at least about ¾ of the diameter of the final spherical implant. Thus if the inert core has a diameter of 2.4 mm, the final sphere will preferably have a diameter of 3.2 mm or less, but greater, of course, than 2.4 mm. By "substantially constant" rate of release is meant that the rate of release decreases by less than about 50% from the start of the implantation to the termination of the release of drug.

A multi layer pellet may be employed to assist in maintaining a substantially constant rate of release per sphere especially if the diameter of the inert core is between 50%–75% of the diameter of the final sphere. In this aspect of the invention it is possible to compensate for the slight decrease in release rate per sphere which results as the diameter of the sphere decrease by adjusting the composition of the coating so that the active ingredient is released at a greater rate per unit area as the radius decreases. For example, this can be performed by using a multi-layer technique wherein, for example, the percentage of water soluble components such as polyethylene glycol is altered so that there are higher concentrations in the inner layers to increase the dissolution rate and compensate for the decrease in surface area. But even with this alternative multi-layer technique it is preferable to utilize an inert inner core which accounts for at least half of the radius of the implanted sphere.

As disclosed previously the inert core may be about 2–10 mm in diameter and preferably about 2–3 mm. The finished sphere having the uniform coating covering the inert core will generally be about 2.1–12 mm in diameter and preferably will be about 2.2 to about 3.5 mm. Thus, the uniform layer (or layers as the case may be) adhering to the inert core will range from about 0.05 mm to about 2 mm thick and preferably will be about 0.1 mm to about 0.5 mm thick. For example if the inert core is 2.0 mm in diameter (1.0 mm radius) and the uniform layer is 0.05 mm, the diameter of the finished sphere is 2.1 mm (2[1.0 + 0.05] = 2.1).

In order to obtain the constant rate of release in the inert core pellet, a coating having a substantially uniform thickness is layered on to the inert spherical core. It is important that the thickness of the coating be substantially uniform around the inert core so that the calculated rate of release will be obtained. Further, it is important that the coating intimately adheres to the core to maintain structural integrity and prevent the release rate from fluctuating. "Intimately adhering" to the core means that the coating layer will stay on the inert core during the entire time period during which the drug is to be released in a manner so that substantially none of the coating falls off to adversely effect the rate of release of this drug.

The coating containing the drug must completely cover the inert core so that the rate of release calculated for the size sphere employed can be obtained. Also, if the inert sphere is not completely covered by the coating containing drug there is a greater likelihood that the coating will deteriorate and be separated from the inert sphere. This of course would adversely effect the rate of release and instead of giving a constant rate would result in a varying rate.

Generally, the process for preparing the spherical, inert core, pellet implant which is a preferred aspect of this invention may be performed by any of the film coating techniques known in the art including the Wurster Air Suspension Coating method, the spray pan method, fluid bed or a programmed automated spray pan method. These processes are broadly discussed in Chapter 88 of Remington's Pharmaceutical Sciences, 14th Edition, Mack Publishing Company, 1970, pp, 1685–1688 and as much of that disclosure as is pertinent is incorporated herein by reference.

Broadly stated, the process involves dissolving the drug and carrier in a suitable solvent, contacting the inert spheres with the resulting solution to thoroughly wet the spheres, then evaporating the solvent from the solution so that the carrier and drug combination remains coated on the inert spheres. Thus, the dromostanolone propionate/carrier combination which is to be coated onto an inert sphere must have solution properties in a solvent or combination of solvents suitable for spray coating. Generally high formulation concentrations in the coating solvent have the advantage of a shorter coating time and use of less solvent, but high formulation concentrations tend to yield a less uniform product and thus it is preferable to use lower concentrations. Generally the concentration of the drug and carrier will be less than 50% and preferably will be between about 15%w ito 25%w in the solvent.

During the coating process the spheres used for the inert cores are kept in constant movement so that the drug/carrier solution is uniformly coated on the spheres, then the solvent is removed by evaporation, generally blowing hot air across the spheres while keeping them in constant motion, again to assure uniformity of coating. The spheres are kept in constant motion by employing a coating pan which is constantly and uniformly revolved at a uniform rate or by using an air suspension column in which the spheres are suspended in an air stream. The solvent is applied intermittently along with the hot air in a pre-set spary/dry cycle.

The coating solvent is important in the process of this invention since it must have the proper solubility characteristics for the formulation as well as the proper drying characteristics to provide smoothness and uniformity of the coating. Examples of acceptable coating solvents for coating are acetone, chloroform, methylene chloride, isopropyl alcohol, ethanol, methanol, propanol, t-butanol tetrahydrofuran, trichloroethylene, dioxane, dimethylformamide, and mixtures of these. It has been discovered that the process is greatly improved and results in a superior product if the solvent combination employed exhibits a boiling point of 59° to 66.4° C. Particularly valuable when using a PEG 6000–7500 is the combination of chloroform and isopropyl alcohol (IPA) at a ratio of about 1:4 to 2:1, preferably about 1:3 to about 1:1, respectively, the drug and PEG being dissolved in the chloroform first and the IPA being added thereafter.

PROCESS OF PRODUCING WEIGHT GAIN IN ANIMALS

The process of producing a greaer than normal weight gain in animals according to this invention comprises implanting the above described subcutaneously implantable pellet of this invention for the desired time period and feeding the animals appropriately.

The basic premise behind the use of an anabolic agent in a domestic stock animal is that the animal will gain more weight during a given time period by using the anabolic agent.

The weight gain may be due to increased consumption by the animal, increased food efficiency, or both. Increased consumption is advantageous, especially to a feed lot operator, since he is trying to maximize the weight gain over a specific time period and is willing to feed the animals greater quantities of food over a shorter period of time if they will fatten faster. Increased consumption may be seen using the implantable pellet of this invention, especially with male animals. Food efficiency (%) is defined as $$\frac{\text{weight gained by animal}}{\text{food consumed by animal}} \times 100\% .$$

Thus the process of producing a weight gain may be a process for increasing the food efficiency of the animal. The commercial advantage of an anabolic agent which increases food efficiency, such as the subcutaneously implantable pellet of this invention, is that it allows a raiser of cattle, sheep, pigs, and the like to produce more marketable meat from the feed purchased. Increased food efficiency will generally be seen in the female animals, e.g. heifers, using the implant pellet of this invention.

The process for producing a weight gain is most useful for domestic stock animals, either before or after sexual maturation particularly ruminants such as cattle, sheep, and the like, but is also valuable for producing weight gain in non-ruminants such as pigs and others. In ruminant animals such as cattle which exhibit growth throughout their life, the pellet implant of this invention may be implanted during any phase of the animal's life and a weight gain greater than normal may be realized. Thus the process of this invention is adaptable to the custom of the cattle raiser concerned. For example, in the case of raising "vealers", calves raised and slaughtered prior to sexual maturity to produce veal, the pellet is implanted in the calf early in its life and the calf is fed and maintained for the necessary period of time after which it is slaughtered. The calf as treated will show a rate of growth which is greater than a calf which has not received an implant. The pellet of this invention appears to be particularly valuable for use in female range calves since not only is the weight increased, but also the calves are prevented from getting pregnant. On the other hand the pellet of this invention may be implanted in a cow which is past puberty and a greater than normal weight gain will also be seen. Such post-puberty cattle include dairy cattle, beef cattle, or crossbreeds of the two. For example, the use to fatten "cull cows" quickly is indicated. A "cull cow" is an animal which may be a dairy or beef cow or cross which is used as a breeder or dairy cow, but at the end of its productive diary life or breeding life, it is fattened and used for beef. The pellet of this invention lends itself well to the process of fattening cull cows by implanting the pellet and feeding the cow its normal diet.

A particularly large weight increase is seen when a pellet of this invention is implanted in an undernourished animal and thereafter the animal is brought onto a normal diet. Although it is generally true that when an undernourished animal is brought onto a normal diet, there is a greater rate of weight gain than in a comparable normal animal, the undernourished animal never seems to reach the same weight and size of the normal animal. Surprisingly, it now appears that by implanting the pellet of this invention in the undernourished animal, it may be brought up to the same weight and size and even surpass a comparable normal animal. This is of great importance and advantage to cattle raisers who may be forced to feed their animals less than a normal nourishing amount over a short, or even extended time period due to uncooperative weather, untoward financial conditions, unproductive gazing range, or other reasons. Thus, another aspect of the process of this invention comprises maintaining a domestic animal on a subnormal diet so that the growth of the animal is less than normal and thereafter implanting the animal with at least one dromostanolone propionate implant pellet while feeding the animal a normal diet, to produce a weight gain which is greater than the weight gain would be without the pellet.

The subcutaneously implantable pellet of this invention is also available for producing a greater than normal weight increase in lambs and pigs, i.e. young sheep and swine not yet sexually mature.

Because of the accuracy of administration the subcutaneously implantable pellet employed in the preferred process of this invention is a pellet implant which exhibits a substantially constant rate of drug release over a first period of time and an abrupt termination of said release at the end of time is employed. Thus the process for producing a greater than normal weight gain in an animal comprises subcutaneously implanting a dromostanolone propionate pellet so that a therapeutically effective amount of the drug is released to the animal at a substantially constant rate over a first time period and a substantially abrupt termination of drug release at the end of the first time period and feeding the animal an appropriate diet. The animal is then maintained for a second period of time subsequent to the first period without removing the pellet, substantially no drug being released during said second period.

Although any pellet design, which releases drug at a substantially constant rate may be employed in the preferred process of this invention, a particularly valuable design is the preferred pellet discussed hereinbefore, i.e. wherein the implantable pellet is spherical and comprises a biocompatible inert spherical core having a diameter of about 2.0 mm. to about 10.0 mm. and a biocompatible, biosoluble coating having a substantially uniform thickness of about 0.05 mm. to about 1.0 mm. intimately adhering to and completely covering the inert spherical core. The composition of the coating may comprise about 5% weight to about 99% weight of a pharmaceutically suitable carrier as described above and about 1% by weight to about 95% by weight of dromostanolone propionate. The process is particularly effective wherein the carrier is a dissolution rate modifier such as polyethylene glycol having a molecular weight of about 3000 to about 20,000, especially PEG 6000–7500, and the inert core is a sphere having a diameter of about 2.0 mm. to about 3.0 mm. and the coating is about 0.1 mm. to about 0.5 mm. in thickness. The second period of time is employed to assure that the drug is entirely metabolized by the animal. If the inert core is absorbed by the animal, the absorption may take place during this time period. The animal may be then slaughtered at the end of the second period of time. This second period of time may be anywhere from 1 to 100 days depending upon the metabolism of the animal and facilities available for holding the animal.

Implantation is done by any method known to be useful for subcutaneous implantation and may be either surgically as taught in U.S. Pat. No. 3,499,445 or merely by injection using a needle implanter such as that taught in U.S. Pat. No. 2,761,446. The spherical pellets of this invention lend themselves to ready injection using the needle type implanter. Generally the pellets will be injected into an area in the animal which will not physically harm or bother the animal's eating habits. For example in the case of heifers and steers the pellets are injected into the animals ears, neck, dewlap, or back regions. In the case where the inert core is a non-dissolving material, it is preferred to inject the spheres in a part of the animal which is easily removed prior to or at slaughter, e.g. the ears or dewlap. On the other hand, if the inert core is of a biosoluble material, the spheres may be implanted elsewhere, e.g. the back, since the core will be absorbed prior to slaughter anyway.

A therapeutically effective amount of dromostanolone propionate is the amount administered which results in a greater than normal weight gain in the animal treated. The amount administered will depend on the sensitivity of the animals treated, ruminants appearing to be substantially more sensitive than nonruminants. A representative effective daily dose for a heifer is about 3 mg dromostanolone propionate per 250 kg of body weight (about 0.012 mg/kg/day). This dosage, will vary from species to species and is not to be interpreted as the optimum in every case for all ruminants. On the other hand a representative effective daily dose for a non-ruminant may be about 2–5 mg/kg/day, but this level, too, may vary from species to species. Because a single pellet is generally not sufficient to provide the therapeutically effective amount for larger animals such as cows, pigs, sheep, and the like, generally it is preferable to inject a plurality of the pellets of this invention. The number of pellets employed will depend on the size of the pellet, the dissolution rate modifier used to form the pellet, the size of the animal, and the type of animal. Thus, anywhere between 5 and 100 pellets may be injected into an animal at one time. Generally, if the same number of pellets of the same formulation are injected into the same species of animal the release rate and the termination will be the same, with allowance for small variations (e.g. less than 5%) between individual animals.

The greater than normal weight gain using the dromostanolone propionate implant hereinbefore described occurs if the animal is fed an appropriate diet it would receive under the usual circumstances where the animal is being readied for market. For example, steers implanted with the pellet of this invention consume more and thus would be feed more for the duration of the period, while heifers may take only a normal diet if the food efficiency is increased. Thus the amount will depend on the animal treated and generally is determined by practice in the art.

The substantially constant rate attained by using the preferred implant pellet design of this invention is a rate which does not change by more than about 50% from the time of implantation to the abrupt termination of drug release. Thus, in the case where the animal is being administered about 0.010 mg/kg/day the rate may drop to about 0.005 mg/kg/day by the termination of drug release, over, e.g. a 60 day period.

PROCESS FOR ESTRUS SUPRESSION AND SYNCHRONIZATION

The process for the supression of estrus according to this invention involves subcutaneously implanting the pellet described hereinbefore so that a therapeutical amount of the drug is released in the animal which is sufficient to prevent the animal from coming into estrus. Preferably the pellet employed releases a substantially constant rate of the active ingredient during a first period of time and abruptly terminates the release of the active ingredient at the end off the first period of time. The process is applicable to female domestic stock animals such as heifers, female calves, sows, sheep, horses and the like, as well as domestic animals such as dogs, cats, hamsters, and the like.

The economic advantage of synchronizing the time when a herd of female domestic animals such as heifers go into estrus has been discussed in U.S. Pat. No. 3,449,445 and as much of that patent disclosure as is pertinent is incorporated herein by reference. As mentioned previously one of the advantages of the process of this invention is that while estrus is suppressed the animal may also gain weight during the same time.

The process of this invention is particularly applicable to preventing the onset of estrus in range fed animals which are out of sight and control of the cattle raiser. For example pre-puberty cows may be implanted so that a substantially constant rate of dromostanolone propionate is released during the first time period while the animals are range fed out of sight and control of the cattle raiser. The animals would normally reach estrus on the range and could be bred during the range feeding. The pellet would prevent that from occurring. The animals are brought back either shortly before or shortly after the release of the drug is terminated then maintained for a second period during which time the animal is allowed to come into estrus. The animals then are inseminated either by natural or preferably artificial means so that the calves may be born at the proper time. Thus, the advantages of synchronization are obtained with the process of this invention and the cattle raiser need not exercise constant supervision over long periods of time of the animal as it sexually matures. On the other hand, it may be imperative that the animal not get pregnant at all, e.g. prior to coming into a feed lot. Of course, the use of the pellet implant of this invention results in a weight gain in the animal as well as the suppression of estrus when the animal matures sexually.

On the other hand, a herd of sexually mature heifers may be implanted with the pellet of this invention and maintained for a first period of time during which time a constant rate of dromostanolone propionate is released and at the end of which period of time there is an abrupt termination of the release of the drug. The animals are collected in one place at the end of the first period of time or shortly before and held for a second period of time during which the animals are allowed to come into estrus. Insemination follows.

The implant and process of this invention may be used in preventing cats, dogs, and other animals from coming into heat. In this case the dromostanolone implant has the advantage of not producing any weight gain at the level used, a surprising result in view of the accompanying weight gain in ruminants.

The following examples are given by way of illustration of the various aspects of this invention but are not to be interpreted as limiting the scope of the invention set forth in the claims of this application.

solution until the PEG was dissolved. 104 ml of isopropyl alcohol were then added to the resulting mixture. This solution was then used to coat 30 g of cellulose acetate spheres, each sphere having an average diameter of 2.5 millimeters (mm) and an average weight of 10.5 milligrams (mg). The spheres were coated in a 5 inch glass coating pan using a Badger air atomization spray gun, a hot air blower and a dual timer. The air pressure of the spray gun was set at 30 pounds per square inch while the pan bed temperature was set at 37° C, pan rotation was 36 revolutions per minute (rpm) and the spray dry cycle was 5 seconds:15 seconds. 10.0 mg of the PEG 6000/Dromostanolone propionate was coated on each sphere.

The resulting spheres were then implanted in heifers as follows:

Four heifers were chosen and divided into 2 groups, group A and group B. The heifers in group A weighed 510 and 562 pounds at the start of the experiment while those in group B weighed 581 and 542 pounds. Both groups of hiefers were kept during the pretreatment period of 56 days under similar conditions. All 4 animals were housed in one pen along with a "teaser" bull and were fed ad lib hay, ad lib access to pasture, and supplemented with 50 lbs. concentrate/pen/day.

WEIGHT GAIN

Group A (No. 1 and 4) was then implanted subcutaneously with 64 of the pellet implants per animal in the animals backs, while group B (No. 2 and 3) was not implanted. The average daily gain (ADG) was then calculated for each group over the next 112 days. Group A (implanted) showed an ADG 53.8% greater than the pretreatment period while group B showed about the same ADG compared to the pretreatment period. Both groups A and group B were then subjected to a washout period of 42 days during which time any drug that would be present in group A would have been washed through the animal system. At the end of the 42 day washout period, group B (No. 2 and 3) was then implanted similarly to group A, but group A (No. 1 and 4) remained untreated and the average daily weight gain was again gathered for each of the animals. During the second period which amounted to 56 days the data showed that the implanted group, group B, had a 53% gain over the washout period, compared with the unimplanted group A which showed about the same ADG as the washout period. The weight gain results are set forth in Tables I, II and III.

Table I

| | | Average Daily Gain (ADG-lbs/day) | | | | |
|---|---|---|---|---|---|---|
| Starting Wt.lbs. | ADG Pre Treat (56 day period) | Implant | ADG-1 112 days | ADG Washout (42 day period) | Implant | ADG-2 56 days |
| A-1-510 4-562 | 1.19 | Yes | 1.83 | 1.43 | No | 1.14 |
| B-2-581 3-542 | 1.09 | No | 1.04 | 1.17 | Yes | 1.77 |

EXAMPLE I

The preferred subcutaneously implantable, spherical pellet of this invention which is comprised of an inert core coated by a uniform layer of a carrier and dromostanolone propionate is prepared as follows:

20.0 grams (g) of dromostanolone propionate were dissolved in 86 milliliters (ml) of chloroform. 20.0 g of PEG 6000 were stirred into the resulting chloroform Table II

| | Percentage Weight Gains | |
|---|---|---|
| | Period 1 (112 days) % of Pre-treatment Period | Period 2 (56 days) % washout period |
| Group A | 153.8%* | 85.0 |

Table II-continued

| Percentage Weight Gains | | |
|---|---|---|
| | Period 1 (112 days) % of Pre-treatment Period | Period 2 (56 days) % washout period |
| Group B | 95.4% | 153.0* |

*Implanted animals

Table III

| | Weight Gained (lbs) | | | |
|---|---|---|---|---|
| Heifer No. | Preimplant (56 days) | Implant (112 days) | Washout (42 days) | Crossover implant (56 days) |
| 1 | 70 | 211* | 54 | 63 |
| 3 | 62 | 120 | 50 | 104* |
| 2 | 60 | 113 | 48 | 94* |
| 4 | 63 | 198* | 60 | 65 |

From Table I the comparative weight gain for the animals can be calculated and is set forth in Table II which shows that during period one group A which had been implanted with the particularly preferred implant design of this ivnention showed a average daily gain of 153.8% of the average daily gain during the pretreatment period while group B, the untreated group, showed only a 95.4% gain over the pretreatment period. During the second time period group A which was untreated showed a 91.9% average daily weight gain as compared to the washout period while group B which was treated with the implant of this invention showed a average daily gain which was 159% of the washout period for the same group.

ESTRUS SUPPRESSION

During the same period of time the animals were examined for weight gain, they were also examined for estrus suppression. The results are set forth in Table IV.

Table IV

| | Estrus Data | | | |
|---|---|---|---|---|
| Heifer No. | Length of 2* preimplant. cycles | Length of post implant./ control cycles | Length of washout cycles | Length of crossover cycles |
| 1 | 20, 20 days | 104 | 22 | 26,20,19 |
| 3 | 19, 23 | 21,19,20,19,21 | 19 | >63 |
| 2 | 19, 21 | 21,19,19,19,21 | 22 | >59 |
| 4 | 21, 21 | 110 | 22 | 20,22 |

*Corresponds to 56 day Pre-treat period of Table I.

It can be seen that substantially complete estrus suppression during the 112 day implant period is obtained in implanted heifers 1 and 4 with the animal returning to a substantially normal cycle after the release of the drug is terminated. After the washout period heifers 2 and 3 are implanted and substantially complete estrus suppression is obtained for the period examined.

EXAMPLE II

Comparison of Activity of Dromostanolone Propionate by daily single injection versus a pellet implant Propylene glycol (PG) solutions of dromostanolone propionate were prepared for subcutaneous injections into female laboratory rats. Ten rats per group were injected daily with 1 ml PG containing 4, 12, 33, 100, 300, and 900 microgram ($\mu$g) per rat doses of dromostanolone propionate.

Other solutions of dromostanolone propionate in sesame oil and in Government Diluting Fluid were prepared to determine the effect of the liquid carrier on the activity of the active drug.

Pellets comprising dromostanolone propionate in combination with a carrier was prepared so that each pellet contained approximately 27.2 mg of active ingredient. The pellet was prepared by granulating dromostanolone propionate with PEG 6000 using methanol. The granulation was dried and screened. Magnesium stearate was added and the resulting granulation was compressed on a tablet machine using 1/8 inch diameter punches and die. The weight of each pellet was 30.0 mg. The pellets were composed of

| Dromostanolone Propionate | 90.49%w |
|---|---|
| PEG 6000 | 9.06%w |
| Magnesium stearate | 0.45%w |

The release rate of the active ingredient from each pellet was determined and found to be about 100 $\mu$g/pellet for the first 20 days, 75 $\mu$g/pellet for the next 20 days, 40 $\mu$g/pellet for the next 20 days, 10 $\mu$g/pellet for the next 20 days, after which the release was undetectable by the methods used.

Using these pellets, three groups of female rats, each group containing 10 rats, were subcutaneously implanted in the back of neck with 4, 6, and 8 dromostanolone proprionate pellets per animal. A control group of 10 rats had no pellets implanted. The average weight per rat for each group was determined by adding the individual weights of each of the rats in the group together and dividing by the number of rats in the group. Each group of rats was then placed on the same diet and the average weight gain for each group was determined. Also estrus suppression was determined for each group of rats.

The results showed (1) in all of the rats implanted with 4, 6 or 8 pellets there was complete estrus suppression over the entire 18 week study, (2) a substantially greater weight gain in the rats that were implanted over the injected control groups, and (3) in each of the groups of rats that were implanted with the pellet there was an increase in food efficiency over the control group.

(1) Estrus suppression

The minimal effective dose to suppress estrus by daily injection was 300 $\mu$g/rat/day. (Estrus is suppressed if at least 50% of animals treated are in diestrus.)

Since the maximum dosage in the implanted rats having 4 pellets/rat was 400 $\mu$g/rat/day (4 pellets × 100 mg/pellet/day) and that dwindled to less than about 40 $\mu$g after 60 days, it appears that the pellet is substantially, and surprisingly, more effective than a daily injection. It should be noted than the maximum delivery in the case of 8 pellets was 800 $\mu$g/rat/day which dropped to less than about 80 $\mu$g/rat/day after about 80 days, estrus being suppressed, however, during the entire 126 day test period.

It was found that dromostanolone propionate in sesame oil or government diluting fluid (GDF) was even less effective than the PG solution. In the case of sesame oil 10 mg (10,000 $\mu$g)/ml/rat was needed for 100% suppression, whereas 3 mg (3000 μg)/ml/rat was required per day in GDF. The results are tabulated in Table IVA.

Table IVA

| | Estrus Suppression | | | | | |
|---|---|---|---|---|---|---|
| | Daily Injection | | | Pellet | | |
| Total Daily Dose (μg) | PG | Days 50% of animals in diestrus Sesame Oil | GDF | No. Pellets (Total Daily Dose) | Days 50% in Diestrus | |
| 0 | 0 | — | — | 0 | | |
| 4 | 0 | — | — | 4(400μg–<40μg) | 98/126 | |
| 12 | 0 | — | — | 6(600–<60) | 126/126 | |
| 33 | 0 | — | — | 8(800–<60) | 126/126 | |
| 100 | 0 | — | — | | | |
| 150 | — | 0 | — | | | |
| 300 | Duration* | 0 | — | | | |
| 900 | " | 0 | — | | | |
| 1100 | — | 0 | — | | | |
| 3000 | — | 0 | Duration* | | | |
| 10,000 | — | Duration* | — | | | |

*Duration of daily dosing (2) Weight gain

The following tables, V, VI, and VII set forth the comparative weight gain data for the rats treated by implantation or injection.

Table V

| | Mean Body Weights of Rats with pellets Dose (Pellets) | | | |
|---|---|---|---|---|
| Weeks | 0 | 4 | 6 | 8 |
| 0 | 137.3 | 135.7 | 134.6 | 134.3 |
| 3 | 222.1 | 240.4 | 235.8 | 239.1 |
| 6 | 268.7 | 300.1 | 288.2 | 292.6 |
| 8 | 287.1 | 324.0 | 310.4 | 320.2 |
| 12 | 299.9 | 353.9 | 334.5 | 343.3 |
| 18 | 321.3 | 386.6 | 344.6 | 374.3 |

Table VI

| | Mean Body Weights of Rats Receiving daily PG Injections Dose (μg) | | | | | |
|---|---|---|---|---|---|---|
| Week | PG Only | 4 | 12 | 33 | 100 | 300 | 900 |
| 0 | 158.0 | 158.2 | 157.6 | 158.6 | 160.8 | 158.0 | 157.7 |
| 3 | 215.6 | 216.5 | 224.0 | 222.9 | 223.2 | 255.6 | 251.7 |
| 6 | 242.4 | — | — | — | — | 279.8 | 280.6 |
| 8 | 259.6 | — | — | — | — | 291.2 | 288.8 |

Table VII

| | % Increase Weight* (over Controls) in Post-Puberal Female Rats | | | | | | | |
|---|---|---|---|---|---|---|---|---|
| | Pellet Dose | | | Injection Dose (μg/day) | | | | |
| Week | 4 | 6 | 8 | 4 | 12 | 33 | 100 | 300 | 900 |
| 3 | 8.3 | 6.2 | 7.8 | 4 | 4.0 | 3.4 | 4.0 | 18.6 | 16.9 |
| 6 | 11.8 | 7.3 | 8.7 | — | — | — | — | 15.5 | 15.8 |
| 8 | 12.9 | 8.2 | 11.6 | — | — | — | — | 12.1 | 11.2 |
| 12 | 17.8 | 11.5 | 14.4 | — | — | — | — | — | — |
| 18 | 20.4 | 7.2 | 16.5 | — | — | — | — | — | — |

*% Increased Weight = $\frac{\text{Treated Wt.} - \text{Control Wt.}}{\text{Control Wt.}} \times 100\%$ From the above data it may be seen that although the daily injection doses of 300 and 900 μg/day result initially in a greater % increased weight, the % increase rapidly drops off. In the animals treated by pellet implantation, on the other hand, % increase in weight increases substantially over the 12 week period for all pellet dose levels and continues to increase over the 18 week period for the 4 and 8 pellet dosage. This is truly surprising since the rate of release in the pellet is decreasing over the period of time while the daily injection is kept constant.

(3) Food Efficiency

Importantly in all rats treated by pellet implantation there was a substantial increase in % food efficiency over the 18 week treatment period of between 11 and 25% over the control group, as set forth in Table VIII.

Table VIII

| | % Food Efficiency-Implanted Animals | | | |
|---|---|---|---|---|
| | | Dose — Pellets | | |
| Control | 4 | 6 | 8 | |
| 7.8% | 9.8 | 8.7 | 9.3 | |

The food efficiency of the animals treated by daily injection was not determined.

EXAMPLE III

Oral Activity of Dromostanolone Propionate

Solutions of dromostanolone propionate in propylene glycol were orally administered daily by gavage for two weeks at doses of 0.7, 2, and 6 milligrams/rat/day, each dose level being given to 10 rats. Only the 6 mg. dose showed any effect, consisting of 3 days of estrus suppression and a 7% increase in body weight after 2 weeks of dosing. Surprisingly, the 6 mg./day dose is substantially more than required for minimum effect using a pellet implant (400–40 μg./day) or subcutaneous injection (300 μg.day). Thus, no further work was done on oral administration of the drug.

EXAMPLE IV

Preparation and Implantation of Preferred Inert Core Formulations of the Pellet of This Invention The solid compressed pellet utilized in Example 2 which gave the superior percent increased weight over the drug given orally or by daily injection produced a long lasting estrus suppression and increased weight gain. However, when the release rate finally drops so low that the pellets are no longer having much effect, there may still be a great deal of drug remaining in the pellet, the drug being unabsorbed by the animal. In order to reduce this wasted material, the preferred formulation of this invention is utilized. The preferred formulation is an inert spherical core with a layer of the drug and a specific carrier intimately adhering to and uniformly coating the inert sphere. Such a combination exhibits a substantially constant rate of release over a first time period and a substantially abrupt termination of release at the end of that time period. By varying the ratio of dromostanolone propionate to the carrier, for example, PEG 6,000, an implant may be fabricated for a particular release rate and duration. Generally an increase in the PEG 6,000 concentration results in an increase in the dissolution rate and has a shorter rate of dissolution. Thus, using PEG 6,000 and dromostanolone propionate to coat the inert spheres, formulations containing 90%, 80%, 50%, 40% and 30% dromostanolone propionate in the coating were prepared. The coated spheres were prepared by dissolving a measured amount of dromostanolone propionate in chloroform and adding the required amount of PEG 6,000 to the resulting chloroform solution until all of the PEG was dissolved. Thereafter, isopropyl alcohol was added to the resulting mixture. This solution was then used to coat cellulose acetate spheres, each sphere having a diameter of 2.5 millimeters and an average weight of 10.5 milligrams. The spheres were coated in a 5 inch glass coating pan using a Badger air atomizer spray gun, a hot air blower, and a dual timer. The air pressure of the spray gun was set at 30 pounds psi while the pan bed temperature was set at 37° C, pan rotation was 36 rpm and the spray dry cycle was 5 seconds; 15 seconds. Table IX-A gives the preparation parameters, while Table IX-B sets forth the resulting characteristics of the preferred coated inert core formulations of this invention.

TABLE IX-A

Preparation Parameters for Coated Inert Core Spheres

| Gm.D.P.* | ml CHCl₃ | g PEG 6000 | ml IPA | g spheres coated | DP* in coating |
|---|---|---|---|---|---|
| 18 | 25 | 2 | 75 | 15 | 90 |
| 16 | 25 | 4 | 75 | 15 | 80 |
| 10 | 25 | 10 | 75 | 15 | 50 |
| 20 | 62.5 | 30 | 187.5 | 30 | 40 |
| 6 | 25 | 14 | 75 | 15 | 30 |

*D.P.=dromostanolone propionate

TABLE IX-B

Resulting Characteristics For Coated Inert Spheres

| %D.P.* | Diameter Inert Core Sphere (mm) | Diameter Coated Sphere (mm) | Total Wt. of Coating (mg) | Density of coating (Calculated) | Total Wt. D.P.* (mg) |
|---|---|---|---|---|---|
| 90 | 2.5 | 3.26 | 9.5 | 0.95 | 8.6 |
| 80 | 2.5 | 3.32 | 10.9 | 0.99 | 8.7 |
| 50 | 2.5 | 3.19 | 9.73 | 1.10 | 4.9 |
| 40 | 2.5 | 3.15 | 8.85 | 1.08 | 3.5 |
| 30 | 2.5 | 3.28 | 11.35 | 1.10 | 3.5 |
| 90** | | | | | 27.2 |

*D.P.=dromostanolone propionate
**Compressed pellet from Example II

Studies were carried on to determine the release rate for the coated spheres. Four spheres coated with mixtures of dromostanolone propionate and PEG 6,000 containing 90, 80, 50, 40, or 30 percent dromostanolone propionate were implanted subcutaneously in post puberal, Simonsen Albino female rats with 5 rats per group. 5 rats were sacrificed every 2 weeks and the implanted pellets were analyzed for composition. From this information the average release rate (dissolution rate) for each pellet was determined and found to be substantially constant over the entire 18 week study. The results are set forth in Table X.

TABLE X

Dissolution Rate Data From Sphere Implants

| Percent RS-1567 | Dissolution Rate (MG CM⁻²DA⁻¹) |
|---|---|
| 90 | 0.098 |
| 80 | 0.161 |
| 50 | 0.377 |
| 40 | 0.804 |
| 30 | 3.06 |

One, Two, four and eight spheres, prepared as described in this example containing 90, 80, 50, 40 or 30% dromostanolone propionate, were implanted subcutaneously in postpuberal, Simonsen Albino, female rats with 10 rats per group. The vaginal cytology was checked daily and body weights recorded once a week for 18 weeks.

ESTRUS SUPPRESSION

Table XI summarizes the effect on vaginal cycling.

TABLE XI

Summary Of The Cycling Effects Of D.P.* Coated Spheres
Days Till 50% of Animals Show Estrus or Proestrus

| Dose | 30% | 40% | 50% | 80 | 90% | 90%** |
|---|---|---|---|---|---|---|
| 1 sphere | 10 | 13 | 9 | 8 | 7 | — |
| 2 spheres | 12 | 32 | 19 | 13 | 14 | — |
| 4 spheres | 10 | 35 | 89 | 29 | 50 | 100 |
| 8 spheres | 13 | 43 | 122 | >126 | >126 | >126 |

*D.P.=dromostanolone propionate
**Comprensed pellet Ex. II

From Table XI it can be seen that 8 spheres with coatings of 50, 80 and 90 percent dromostanolone propionate maintained estrus suppression for at least 18 weeks, and were comparable to 8 spheres of solid dromostanolone propionate pellets (90%). This is a surprising result in that the compressed dromostanolone propionate pellets contain more than 3 times the amount of active drug as the 80 or 90% coated inert spheres. Thus, it appears that the pellets of about 50%–90% drug are particularly effective.

WEIGHT GAIN

Tables XIII and XIV show percent increased weight control animals. Table XII summarizes the body weight effects.

TABLE XII

Summary Of Increased Weight Effects Of Dromostanolone
Propionate Coated Spheres In The Rat Comparing
The Percentage Drug In The Sphere Coating

| % D.P.* In Coating Material | Number of spheres | Maximum increased weight over controls and comment on duration of effect |
|---|---|---|
| 90% (Compressed Pellet) | 4 | 21% still increasing at 18 weeks |
| | 8 | 17% still increasing at 18 weeks |
| 90% | 4 | 26% still increasing at 18 weeks |
| | 8 | 23% still increasing at 18 weeks |
| 80% | 4 | 21% maximum at 9 weeks, maintained |

TABLE XII-continued

Summary Of Increased Weight Effects Of Dromostanolone Propionate Coated Spheres In The Rat Comparing The Percentage Drug In The Sphere Coating

| % D.P.* In Coating Material | Number of spheres | Maximum increased weight over controls and comment on duration of effect |
|---|---|---|
| | 8 | 32% still increasing at 18 weeks |
| 50% | 4 | 17% maximum at 6 weeks, maintained thereafter |
| | 8 | 18% maximum at 6 weeks, maintained thereafter |
| 40% | 4 | 13% maximum at 5 weeks, then gradual decrease |
| | 8 | 10% maximum at 3 weeks, then gradual decrease |
| 30% | 4 | 7% maximum at 2 weeks, then rapid decrease |
| | 8 | 5% maximum at 2 weeks, then rapid decrease |

*D.P.=dromostanolone propionate

TABLE XIII

Mean Body Weights

| Dose (% D.P.*-No. pellets) | Weeks After Implantation | | | | | |
|---|---|---|---|---|---|---|
| | 0 | 3 | 6 | 8 | 12 | 18 |
| 30% —0 | 146.6 | 220.6 | 257.8 | — | — | — |
| —1 | 148.3 | 228.6 | 261.5 | — | — | — |
| —2 | 148.5 | 234.6 | 269.4 | — | — | — |
| —4 | 146.2 | 231.8 | 261.4 | — | — | — |
| —8 | 147.5 | 230.2 | 262.4 | — | — | — |
| 40% —0 | 141.4 | 221.2 | 258.5 | 272.7 | — | — |
| —1 | 139.5 | 247.8 | 282.2 | 297.8 | — | — |
| —2 | 140.3 | 250.5 | 288.8 | 299.4 | — | — |
| —4 | 142.3 | 248.4 | 290.6 | 303.5 | — | — |
| —8 | 143.5 | 245.1 | 277.3 | 294.0 | — | — |
| 50% —0 | 136.6 | 214.1 | 253.3 | 265.9 | 291.5 | 314.6 |
| —1 | 136.2 | 231.5 | 283.4 | 297.9 | 309.4 | 344.4 |
| —2 | 136.8 | 240.6 | 297.5 | 312.0 | 341.2 | 361.9 |
| —4 | 137.4 | 242.4 | 296.4 | 309.0 | 336.4 | 357.0 |
| —8 | 137.9 | 245.4 | 298.8 | 311.7 | 345.0 | 373.5 |
| 80% —0 | 136.6 | 214.1 | 253.3 | 265.9 | 291.5 | 314.6 |
| —1 | 139.7 | 227.9 | 273.0 | 286.7 | 310.4 | 328.1 |
| —2 | 135.4 | 225.7 | 268.8 | 282.2 | 304.9 | 330.5 |
| —4 | 138.0 | 243.5 | 300.2 | 317.5 | 348.0 | 374.0 |
| —8 | 138.9 | 257.5 | 320.5 | 337.1 | 374.0 | 413.7 |
| 90% —0 | 140.3 | 208.7 | 246.6 | 258.4 | 276.5 | 289.5 |
| —1 | 142.3 | 227.2 | 264.1 | 278.8 | 302.1 | 323.0 |
| —2 | 143.0 | 225.7 | 266.6 | 280.9 | 304.0 | 323.6 |
| —4 | 143.4 | 242.9 | 293.4 | 311.1 | 333.8 | 356.1 |
| —8 | 143.8 | 239.8 | 295.4 | 313.0 | 334.9 | 364.9 |

*D.P.=dromostanolone propionate

TABLE XIV

% Increase Weight* (Over Controls)

| (% D.P. - No. pellets) | Weeks After Implantation | | | | | |
|---|---|---|---|---|---|---|
| | 0 | 3 | 6 | 8 | 12 | 18 |
| 30% —1 | | 3.6 | 1.4 | — | — | — |
| —2 | | 6.3 | 4.5 | — | — | — |
| —4 | | 5.1 | 1.4 | — | — | — |
| —8 | | 4.4 | 1.8 | — | — | — |
| 40% —1 | | 12.0 | 9.2 | 9.2 | — | — |
| —2 | | 13.2 | 11.8 | 9.8 | — | — |
| —4 | | 12.3 | 12.4 | 11.3 | — | — |
| —8 | | 10.8 | 7.3 | 7.8 | — | — |
| 50% —1 | | 8.1 | 11.8 | 12.0 | — | — |
| —2 | | 12.3 | 17.4 | 17.3 | 17.0 | 15.0 |
| —4 | | 13.2 | 17.0 | 16.2 | 15.4 | 13.8 |
| —8 | | 14.6 | 17.9 | 17.2 | 18.4 | 18.7 |
| 80% —1 | | 6.4 | 7.8 | 7.8 | 6.5 | 4.3 |
| —2 | | 5.4 | 6.1 | 6.1 | 4.6 | 5.1 |
| —4 | | 13.7 | 18.5 | 19.4 | 19.4 | 18.9 |
| —8 | | 20.2 | 26.5 | 26.8 | 28.3 | 31.5 |
| 90% —1 | | 8.9 | 7.1 | 7.9 | 9.3 | 11.6 |
| —2 | | 8.1 | 8.1 | 8.7 | 9.9 | 11.8 |
| —4 | | 16.4 | 19.0 | 20.4 | 20.7 | 23.0 |
| —8 | | 14.9 | 19.8 | 21.1 | 21.1 | 26.0 |

From Table XII it can be seen that the spheres coated with 80 and 90 percent of the dromostanolone propionate produced increases in weight from 21–32 percent over the control. These weight gain effects are equal to or greater than those of the solid dromostanolone propionate used in Example II. Again, these superior and unexpected results despite the fact that the regular compressed pellet implant contains more than three times the amount of drug in the 80 or 90% inert core pellet. Even the rats implanted with 4 and 8 50% inert core pellets showed a maximum increased weight over controls of 17% and 18% at 6 weeks which was maintained thereafter.

It should be noted that weight gain is related to estrus suppression and generally there will be greater weight gain while estrus is suppressed than when the animal is cycling normally that is more active sexually. With the implant of this invention both effects are seen and thus the weight gain will be greater while estrus is suppressed.

TOTAL BODY COMPOSITION

3 Female rats in the control group and 3 female rats having 8 of the 80:20 (drug:CARBOWAX 6000) spheres were sacrificed at 7 weeks to determine whole carcass composition. It was found that there was essentially no difference in total body composition between the control and treated groups, even though the treated group exhibited a substantially greater body weight.

Eighteen weeks after implantation with 80% RS-1567 spheres all rats including controls, were sacrificed and a proximate analysis of whole carcass composition was performed. At the time of sacrifice the rats with 2, 4 and 8 spheres had 5.7%, 18.9% and 32.2% greater body weight than controls, respectively. There was essentially no difference in total body composition between treated groups and controls although there were extreme differences in actual body weights.

EXAMPLE V

Preparation Of Diffusion Matrix Pellet

Ten parts of dromostanolone propionate are thoroughly mixed with Silastic 382 elastomer and 360 medical fluid (Dow-Corning). The curing agent for the elastomer is added and mixed well with the three component mixture. The mixture is then placed in a cylindrical mold and allowed to cure to form a cylinder pellet implant. The implant is 6.2 grams in weight, of which 10% is dromostanolone propionate, 80% silastic elastomer, and 10% medical fluid.

EXAMPLE VI

Preparation Of A Diffusion Barrier Implant 45 mg. of dromostanolone propionate and 45 mg. of polysorbate 80 are mixed well. The mixture is then placed in a Silastic medical grade tubing having an inside diameter of 0.132 inches and an outside diameter of 0.183 inches and being 1.8 cm. in length, the tubing being first sealed at one end with Silastic medical grade adhesive. After filing the tubes, the other is sealed with Silastic medical grade adhesive to form the final product which exhibits a substantially constant rate of drug release.

We claim as our invention:

1. A solid, subcutaneously implantable pellet for producing a greater than normal weight gain in animals and suppressing estrus in female animals, which pellet comprises about 1% to about 99.5% by weight of the 17-propionate of 2$\alpha$-methyl-androstan-17$\beta$-ol-3-one in combination with about 0.5% to about 99% by weight of a biocompatible carrier, said carrier being present in an amount sufficient to maintain the structural integrity of the pellet when implanted in the animal's body.

2. The subcutaneously implantable pellet of claim 1 wherein the shape of the pellet is spherical.

3. The spherical pellet of claim 2 which exhibits a substantially constant rate of delivery over a first time period and an abrupt termination of drug release at the end of said time period, said implant comprising
   a. a biocompatible, inert, spherical core having a diameter of about 2 mm to about 10 mm and
   b. at least one biocompatible, biosoluble coating having a substantially uniform thickness of about 0.05 mm to about 1.0 mm intimately adhering to and completely covering said inert core, the composition of said coating comprising a substantially homogeneous mixture of (i) about 5% weight to about 90% weight of a pharmaceutically suitable carrier and (ii) about 10% weight to about 95% weight of said propionate.

4. The pellet of claim 1 wherein said carrier is chosen from the group consisting of cholesterol, a solid polyethylene glycol, biocompatible high molecular weight fatty acids, solid biosoluble wax, carbomethoxy cellulose, and polyvinylpyrrolidone.

5. The spherical pellet of claim 4 which is spherical and wherein said carrier is a solid polyethylene glycol having a molecular weight of about 3,000 to about 20,000 and said core is cellulose acetate.

6. The spherical pellet of claim 3 wherein said core is a biosoluble substance.

7. A spherical, subcutaneously implantable, solid pellet for producing a greater than normal weight gain in animals and suppressing estrus in female animals, which pellet exhibits a substantially constant rate of drug release delivery over the first time period and an abrupt termination of drug release at the end of said time period, said pellet comprising
   a. a biocompatible, inert, spherical core having a diameter of about 2 mm to about 10 mm, and
   b. a biocompatible, biosoluble coating having a substantially uniform thickness of about 0.05 mm to about 1 mm intimately adhering to and completely covering said inert core, the composition of the coating comprising a substantially homogeneous mixture of (i) about 5% weight to about 80% weight of a carrier which is polyethylene glycol having a molecular weight of about 6,000 to about 7,500, and (ii) about 20% by weight to about 90% by weight of the 17-propionate of 2$\alpha$-methyl-androstan-17$\beta$-ol-3-one, the carrier being present in an amount sufficient to maintain structural integrity of the pellet when implanted in the animal's body.

8. The spherical pellet of claim 7 wherein said inert core has a diameter of about 2 mm to about 3 mm and is cellulose acetate, the diameter of said inert core is at least 75% of the diameter of the implantable pellet, said coating is about 0.1 mm to about 0.5 mm thick and the composition of said coating comprises about 30%w to about 90%w of said propionate and about 10%w to about 70%w of said carrier.

9. A subcutaneously implantable pellet for producing a greater than normal weight gain in animals and suppressing estrus in female animals, which pellet comprises about 1% to about 99.5% weight of the 17-propionate of 2$\alpha$-methyl-androstan-17$\beta$-ol-3-one in combination with and about 0.5% by weight to 99% by weight of a biocompatible carrier which amount is sufficient to maintain the structural integrity of the pellet when implanted in the animal's body said pellet exhibiting a substantially constant rate of release of said propionate when subcutaneously implanted in an animal over a first time period.

10. The pellet of claim 9 comprising said 17-propionate enclosed in a capsule of silicone rubber and being a diffusion barrier type, said propionate being capable of diffusing through said silicone rubber to the outer surface of said capsule at a constant rate.

11. A process for producing weight gain in animals which is greater than normal, which process comprises subcutaneously implanting at least one solid pellet which comprises about 1% by weight to about 99.5% by weight of the 17-propionate of 2$\alpha$-methyl-androstan-17b-ol-3-one in combination with about 0.5% by weight to 99% by weight of a biocompatible carrier so that a weight gain producing amount is released to said animal and feeding said animal on a normal diet, said carrier being present in an amount which is sufficient to maintain the structural integrity of the pellet when implanted in the animal's body.

12. The process of claim 11 wherein a plurality of pellets are implanted in said animal.

13. The process of claim 11 wherein said carrier is a solid polyethylene glycol having a molecular weight of about 3,000 to about 20,000.

14. The process of claim 11 wherein said implant exhibits a substantially constant rate of drug delivery over a first time period and an abrupt termination of drug release at the end of said time period.

15. The process of claim 14 wherein said pellet is spherical and comprises a. a biocompatible, inert, spherical core having a diameter of about 2.0 mm to about 10.0 mm, and b. a biocompatible, biosoluble coating having a substantially uniform thickness of about 0.05 mm to about 1.0 mm intimately adhering to and completely covering said inert core, the composition of the coating comprising a substantially homogeneous mixture of (i) about 5% weight to about 90% weight of a pharmaceutically suitable carrier and (ii) about 10% by weight to about 95% by weight of said propionate.

16. The process of claim 15 wherein said carrier is a polyethylene glycol having a molecular weight of about 6000 to 7500 and said inert core is a cellulose acetate sphere having a diameter of about 2.0 mm to about 3.0 mm, said coating has a thickness of about 0.1 mm to about 0.5 mm.

17. The process of claim 11 wherein said animal is a ruminant.

18. The process of claim 17 wherein said ruminant is a heifer and the amount is about 3 milligram per 250 kilograms of live animal weight per day.

19. The process of claim 17 wherein said ruminant is range fed.

20. The process of claim 17 wherein said animal is a steer.

21. The process of claim 11 wherein said animal is a female calf, a ewe lamb, or a gilt and said pellet is implanted prior to the animal's sexual maturity.

22. The process of claim 11 wherein said weight gain producing amount of said propionate is sufficient to suppress estrus as well.

23. A process for producing weight gain in an animal which comprises a. subcutaneously implanting in an animal for a first period of time at least one implant comprising about 1% by weight to about 99.5% by weight of the 17-propionate of 2α-methyl-androstan-17β-ol-one in combination with about 0.5% by weight to 99% by weight of a biocompatible carrier which is sufficient to maintain the structural integrity of the implant when implanted in the animal's body, said propionate being released to the animal in an amount sufficient to effect weight gain, the implant exhibiting a substantially constant rate of release of said propionate over said first period of time, said agent being substantially fully released at the end of said first period of time, b. feeding said animal during said first time period, and c. maintaining said animal for a second period of time subsequent to said first period without removing said implant, substantially none of said agent being released from said implant during said second period of time.

24. The process of claim 23 further including the step of (d) slaughtering said animal at the end of said second period of time.

25. The process of claim 23 wherein said implant is spherical and comprises i. a biocompatible, inert, spherical core having a diameter of about 2 mm to about 10 mm and ii. a biocompatible, biosoluble coating having a substantially uniform thickness of about 0.05 mm to about 1.0 mm intimately adhering to and completely covering said inert core, the composition of said coating comprising a substantially homogeneous mixture of about 5% weight to about 90% weight of a pharmaceutically suitable carrier and 10% weight to about 95% weight of said propionate.

26. The process of claim 25 wherein said inert core is absorbed by the animal during said second time period, and the process further includes the step of (d) slaughtering said animal after the absorption of the inert core by said animal.

27. The process of claim 24 wherein said animal is a heifer, steer, gilt, ewe lamb or female bovine calf.

28. A process of controlling estrus in a female animal which comprises a. subcutaneously implanting in a female animal for a first period of time at least one pellet which comprises about 1% by weight to about 99.5% by weight of the 17-propionate of 2α-methyl-androstan-17β-ol-3-one in combination with about 0.5% by weight to about 1% by weight of a compatible carrier which is sufficient to maintain the structural integrity of said solid pellet when implanted in the animal's body, the pellet exhibiting a substantially constant rate release of said propionate over said first period of time with said agent being fully released at the end of said first period of time, enough of said propionate being released to prevent the animal from coming into heat, thereafter b. allowing the female animal to come into heat after said first period of time without removing said implant, and c. inseminating said female animal.

29. The process of claim 28 wherein a plurality of female animals are implanted with said pellet so that each of the animals is prevented from coming into heat during said first period of time then each of the animals is allowed to come into heat at about the same time and each is then inseminated shortly thereafter.

30. The process of claim 28 wherein the animal is a heifer.

31. The process of claim 29 wherein the animals are heifers.

32. The process of claim 28 wherein said animal is implanted prior to reaching sexual maturity.

33. A process for preventing a female cat or a female dog from coming into heat, which process comprises subcutaneously implanting in said cat or dog at least one pellet which comprises about 1% by weight to about 99.5% by weight of the 17-propionate of 2α-methyl-androstan-17β-ol-3-one in combination with about 0.5% by weight to about 99% by weight of a biocompatible carrier which is sufficient to maintain the structural integrity of said pellet when implanted in the animal's body, the pellet exhibiting a substantially constant rate of release over a first time period, enough of said propionate being released to prevent said cat or dog from coming into heat.

34. The process of claim 33 wherein said implant is spherical and comprises i. a biocompatible, inert, spherical core having a diameter of about 2 mm to about 10 mm, and ii. a biocompatible, biosoluble coating having a substantially uniform thickness of about 0.2 mm to about 1.0 mm intimately adhering to and completely covering said inert core, the composition of said coating comprising a substantially homogeneous mixture of about 5% weight to about 90% weight of a pharmaceutically suitable carrier and 10% weight to about 95% weight of said propionate.

35. A process for producing a greater than normal weight gain in animals or suppressing estrus in female animals by administering the 17-propionate of $2\alpha$-methyl-androstan-$17\beta$-ol-3-one to an animal which process comprises subcutaneously implanting a solid pellet comprising about 1% by weight to about 99.5% by weight of said 17-propionate with about 0.5% by weight to about 99% by weight of a biocompatible carrier which is sufficient to maintain the structural integrity of said solid pellet when implanted in the animal's body, said pellet exhibiting a substantially constant rate of release of weight producing or estrus suppressing amount of said 17-propionate over a time period.

36. The process of claim 35 wherein said pellet comprises said 17-propionate enclosed in a capsule of silicone rubber, said prioionate being capable of diffusing through said silicone rubber to the outer surface of said capsule at a consant rate.

37. The process of claim 35 wherein said implant is spherical and comprises
  i. a biocompatible, inert, spherical core having a diameter of about 2 mm to about 10 mm, and
  ii. a biocompatible, biosoluble coating having a substantially uniform thickness of about 0.2 mm to about 1.0 mm intimately adhering to and completely covering said inert core, the composition of said coating comprising a substantially homogeneous mixture of about 5% weight to about 90% weight of a pharmaceutically suitable carrier and 10% weight to about 95% weight of said propionate.

38. The pellet of claim 10 wherein said capsule contains a mixture of about 50–100% of said propionate and about 0–50% of polysorbate 80.

* * * * *